US010434167B2

(12) United States Patent
Alving et al.

(10) Patent No.: US 10,434,167 B2
(45) Date of Patent: Oct. 8, 2019

(54) NON-TOXIC ADJUVANT FORMULATION COMPRISING A MONOPHOSPHORYL LIPID A (MPLA)-CONTAINING LIPOSOME COMPOSITION AND A SAPONIN

(71) Applicant: The United States of America as Represented by the Secretary of the Army, Washington, DC (US)

(72) Inventors: Carl R. Alving, Bethesda, MD (US); Zoltan Beck, Rockville, MD (US)

(73) Assignee: The Government of the United States as Represented by the Secretary of the Army, Fort Detrick, MD (US)

( * ) Notice: Subject to any disclaimer, the term of this patent is extended or adjusted under 35 U.S.C. 154(b) by 0 days.

(21) Appl. No.: 15/127,081

(22) PCT Filed: Mar. 25, 2015

(86) PCT No.: PCT/US2015/022461
§ 371 (c)(1),
(2) Date: Sep. 19, 2016

(87) PCT Pub. No.: WO2015/148648
PCT Pub. Date: Oct. 1, 2015

(65) Prior Publication Data
US 2017/0182152 A1 Jun. 29, 2017

Related U.S. Application Data
(60) Provisional application No. 61/970,118, filed on Mar. 25, 2014.

(51) Int. Cl.
| | | |
|---|---|---|
| *A61K 9/127* | (2006.01) | |
| *A61K 39/00* | (2006.01) | |
| *A61K 39/21* | (2006.01) | |
| *A61K 39/39* | (2006.01) | |
| *A61K 39/12* | (2006.01) | |
| *C12N 7/00* | (2006.01) | |

(52) U.S. Cl.
CPC ............ *A61K 39/21* (2013.01); *A61K 9/127* (2013.01); *A61K 39/12* (2013.01); *A61K 39/39* (2013.01); *C12N 7/00* (2013.01); *A61K 2039/55555* (2013.01); *A61K 2039/55572* (2013.01); *A61K 2039/55577* (2013.01); *C12N 2740/16034* (2013.01); *C12N 2740/16134* (2013.01); *C12N 2740/16171* (2013.01)

(58) Field of Classification Search
CPC .......... A61K 9/127; A61K 2039/55555; A61K 2039/55577; A61K 2039/55572
See application file for complete search history.

(56) References Cited

U.S. PATENT DOCUMENTS

| | | | |
|---|---|---|---|
| 4,186,183 A | 1/1980 | Steck et al. | |
| 4,302,459 A | 11/1981 | Steck et al. | |
| 4,684,479 A | 8/1987 | D'Arrigo | |
| 5,057,540 A | 10/1991 | Kensil et al. | |
| 5,215,680 A | 6/1993 | D'Arrigo | |
| 5,750,110 A * | 5/1998 | Prieels ................. | A61K 39/015 424/208.1 |
| 5,753,260 A * | 5/1998 | Alving .................. | A61K 9/127 424/184.1 |
| 5,874,104 A | 2/1999 | Adler-Moore et al. | |
| 5,888,519 A | 3/1999 | Alving | |
| 5,916,588 A | 6/1999 | Popescu et al. | |
| 5,965,156 A | 10/1999 | Proffitt et al. | |
| 6,043,094 A | 3/2000 | Martin et al. | |
| 6,056,973 A | 5/2000 | Allen et al. | |
| 6,126,966 A | 10/2000 | Abra et al. | |
| 6,224,902 B1 * | 5/2001 | Alving .................. | A61K 9/127 424/184.1 |
| 6,231,859 B1 | 5/2001 | Kensil | |
| 6,294,191 B1 | 9/2001 | Meers et al. | |
| 6,316,024 B1 | 11/2001 | Allen et al. | |
| 6,322,809 B1 * | 11/2001 | Gregoriadis ........... | A61K 9/127 264/4.1 |
| 6,352,716 B1 | 3/2002 | Janoff et al. | |
| 6,406,713 B1 | 6/2002 | Janoff et al. | |
| 6,506,386 B1 * | 1/2003 | Friede ................... | A61K 39/39 424/184.1 |
| 6,759,057 B1 | 7/2004 | Weiner et al. | |
| 6,846,489 B1 * | 1/2005 | Garcon ................ | A61K 39/015 424/278.1 |
| 2008/0274533 A1 * | 11/2008 | Alving .................. | A61K 39/21 435/235.1 |
| 2011/0206758 A1 | 8/2011 | Vandepapeliere | |
| 2012/0087976 A1 * | 4/2012 | Henderickx .......... | A61K 39/00 424/450 |

FOREIGN PATENT DOCUMENTS

| | | |
|---|---|---|
| WO | WO-94/14454 A1 | 7/1994 |
| WO | WO-96/33739 A1 | 10/1996 |
| WO | WO-2012/088414 A1 | 6/2012 |

OTHER PUBLICATIONS

Leekumjorn et al., Molecular studies of the gel to liquid crystalline phase transition for fully hydrated DPPC and DPPE bilayers, Biochemica et Biophysica Acta, 2007, p. 354-365 (Year: 2007).*

(Continued)

*Primary Examiner* — Bethany P Barham
*Assistant Examiner* — Peter Anthopolos
(74) *Attorney, Agent, or Firm* — Drinker Biddle & Reath LLP

(57) ABSTRACT

Provided herein is an adjuvant formulation comprising a monophosphoryl lipid A (MPLA)-containing liposome composition to saponin (e.g., QS-21), wherein the liposome composition comprises i) a lipid bilayer comprising phospholipids in which the hydrocarbon chains have a melting temperature in water of ≥23° C. and ii) cholesterol at a mole percent concentration of greater than about 50% (mol/mol), preferably about 55% to about 71% (mol/mol), or more preferably about 55% (mol/mol). The adjuvant formulation displays minimal toxicity of either lipid A or saponin.

16 Claims, 12 Drawing Sheets

(56) References Cited

OTHER PUBLICATIONS

Alving, C. R., et al., "Preparation and Use of Liposomes in Immunological Studies," Liposome Technology, 2nd Edition, vol. III, pp. 317-343 (1993).*

Antimisiaris, Sophia G., Pramukh Jayasekera, and Gregory Gregoriadis. "Liposomes as vaccine carriers: incorporation of soluble and particulate antigens in giant vesicles." Journal of immunological methods 166.2 (1993): 271-280.*

Kersten, Gideon FA, and Daan JA Crommelin. "Liposomes and ISCOMS as vaccine formulations." Biochimica et Biophysica Acta BBA)—Reviews on Biomembranes 1241.2 (1995): 117-138.*

Wassef, Nabila M., Carl R. Alving, and Roberta L. Richards. "Liposomes as carriers for vaccines." Immunomethods 4.3 (1994): 217-222.*

Carl R. Alving, et al., "Liposomes containing lipid A: an effective, safe, generic adjuvant system for synthetic vaccines," Expert Rev. Vaccines 11(6), (2012) pp. 733-744.

Zoltan Beck, et al., "Detection of liposomal cholesterol and monophosphoryl lipid A by QS-21 saponin and Limulus polyphemus amebocyte lysate," Biochimica et Biophysica Acta 1848 (2015) 755-780.

Nathalie Garcon, et al., "Recent clinical experience with vaccines using MPL- and QS-21-containing Adjuvant Systems," Expert Review of Vaccines, Expert Reviews Ltd., vol. 10, No. 4, 2011, pp. 471-486.

Donald M. Small, et al., "Handbook of Lipid Research, vol. 4, The Physical Chemistry of Lipids From Alkanes to Phospholipids," Plenum, NY, 1986, pp. 49-50.

International Search Report dated Jun. 18, 2015 for PCT/US2015/022461.

Written Opinion dated Jun. 18, 2015 for PCT/US2015/022461.

Wikipedia page for "Lipid bilayer phase behavior," available at https://en.wikipedia.org/wiki/Lipid_bilayer_phase_behavior.

Silvia, "Quillaia Extracts Type 1 and Type 2," Chemical and Technical Assessment (CTA), FAO, 61st JECFA (2004) (available at http://www.fao.org/fileadmin/templates/agns/pdf/jecfa/cta/61/QUILLAIA.pdf).

Belt, 4 J. Biophys. Biochem. Cytol. 337 (1958).

Mora et al., 67 Atherosclerosis 143 (1987).

Knight et al., 69 Ann. Trop. Med. Parasitol. 197 (1975) (Abstract only).

Bangham et al., 13 J. Mol. Biol. 238 (1965).

Deamer, 24 FASEB J. 1308 (2010).

Vejux et al., 20 J. Nutr. Biochem. 45 (2009).

Small, Handbook of Lipid Research Vo. 4 Plenum, NY, 1986, pp. 510-513.

Hafez et al., 47 Adv. Drug Deliv. Rev. 139 (2001).

Caffrey, 71 Acta. Crystallogr. F Struct. Biol. Commun. 3 (2015).

Office Action issued in European patent application No. 15 716 264.5, dated May 7, 2018.

Zoltan Beck, et al., "Differential immune responses to HIV-1 envelope protein induced by liposomal adjuvant formulations containing monophosphoryl lipid A with or without QS21," Vaccine 33, (2015), pp. 5578-5587.

Gary R. Matyas, et al., "Oil-in-Water Liposomal Emulsions for Vaccine Delivery," Methods in Enzymology, 2003, vol. 373, pp. 34-50.

Singh et al., "Saturated phospholipids are required for nano- to micron-size transformation of cholesterol-containing liposomes upon QS21 addition," Journal of Liposome Research, Nov. 23, 2018:1-4. doi: 10.1080/08982104.2018.1538239.

* cited by examiner

NON-TOXIC ADJUVANT FORMULATION COMPRISING A MONOPHOSPHORYL LIPID A (MPLA)-CONTAINING LIPOSOME COMPOSITION AND A SAPONIN

CROSS REFERENCE TO RELATED APPLICATIONS

This application is the National Stage of International Application No. PCT/US2015/022461, filed Mar. 25, 2015, and claims benefit to U.S. Provisional Application No. 61/970,118 filed Mar. 25, 2014, which is incorporated here in its entirety.

U.S. GOVERNMENT RIGHT

Part of the work performed during development of the embodiments of the present disclosure utilized U.S. government funds through United States Department of Defense Grant No. W81XWH-07-2-0067. The U.S. government has certain rights in the invention.

FIELD

Described herein relates to compositions comprising a monophosphoryl lipid A (MPLA)-containing liposome and at least one saponin, e.g., QS-21. The liposome comprises i) a lipid bilayer comprising phospholipids in which the hydrocarbon chains have a melting temperature in water of ≥23° C. and ii) cholesterol at a mole percent concentration of greater than about 50% (mol/mol).

BACKGROUND

Optimal beneficial effects of many modern vaccines require the use of vaccine adjuvants that enhance the immune response while maintaining systemic safety and minimal side reactions after injection. Lipopolysaccharides (LPS) are the major surface molecule of, and occur exclusively in, the external leaflet of the outer membrane of gram-negative bacteria. LPS impede destruction of bacteria by serum complement and phagocytic cells, and are involved in adherence for colonization. LPS are a group of structurally related complex molecules of approximately 10,000 Daltons that contain lipid A, which is the innermost region of LPS that serves as the hydrophobic anchor and comprises phosphorylated glucosamine disaccharide units carrying long chain fatty acids.

The biological activities of LPS, such as lethal toxicity, pyrogenicity, and adjuvanticity, have been shown to be related to the lipid A moiety. Both LPS and lipid A have long been known for their strong adjuvant effects, but the high toxicity of these molecules has limited their use in vaccine formulations. Significant scientific effort has occurred towards reducing the toxicity of LPS or lipid A while maintaining their adjuvanticity.

Other commonly used non-human adjuvants are *Quillaja* saponins, which are a mixture of amphipathic triterpene glycosides extracted from the bark of the tree *Quillaja saponaria*. Crude saponins have been employed as veterinary adjuvants. Quil-A is a partially purified aqueous extract of the *Quillaja* saponin material, and QS-21 is an HPLC purified fraction of Quil A. Methods of producing QS-21 (referred to as QA21) are disclosed in U.S. Pat. No. 5,057, 540. One of the major side effects of using saponins such as QS-21, however, is its cytotoxicity. Specifically, although the exact cytotoxic mechanism is currently unknown, saponins cause hemolysis, which is the rupturing or lysis of red blood cells.

What is needed is a vaccine delivery composition that includes adjuvants for bolstering the immune response, but without the associated cytotoxicity.

SUMMARY

Accordingly, there remains a need in the field to develop more potent while safer adjuvant formulations. Provided herein is an adjuvant formulation comprising a monophosphoryl lipid A (MPLA)-containing liposome (L(MPLA)) composition and a saponin, wherein the adjuvant formulation displays minimal toxicity of either lipid A or saponin.

Accordingly, provided is an adjuvant formulation comprising a monophosphoryl lipid A (MPLA)-containing liposome composition and at least one saponin, wherein the liposome composition comprises i) a lipid bilayer composing phospholipids in which the hydrocarbon chains have a melting temperature in water of ≥23° C. and ii) cholesterol at a mole percent concentration of greater than about 50% (mol/mol). The saponin may be selected from QS-7, QS-18, QS-21, or a mixture thereof. Preferably, the saponin can be QS-21.

In one aspect, the liposome composition of the adjuvant formulation may comprise cholesterol at a mole percent concentration of about 55% to about 71% (mol/mol), or preferably about 55% (mol/mol). The liposome composition of the adjuvant formulation may comprise a phosphatidylcholine (PC) selected from the group consisting of: dimyristoyl phosphatidylcholine (DMPC), dipalmitoyl phosphatidylcholine (DPPC), and distearyl phosphatidylcholine (DSPC). Alternatively, the liposome composition of the adjuvant formulation may comprise a phosphatidylglycerol (PG) selected from the group consisting of: dimyristoyl phosphatidylglycerol (DMPG), dipalmitoyl phosphatidylglycerol (DPPG), and distearyl phosphatidylglycerol (DSPG). The liposome composition of the adjuvant formulation may have a ratio of the PC to the PG (mol/mol) about 0.5:1, about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1. The liposome composition of the adjuvant formulation may comprise multi-lamellar vesicles (MLV) or small uni-lamellar vesicles (SUV), wherein small uni-lamellar vesicles are about 50 to about 100 nm in diameter, and wherein multi-lamellar vesicles are about 1 to about 4 μm in diameter.

In another aspect, the liposome composition of the adjuvant formulation may comprise about 5 mg or less, about 4 mg or less, about 3 mg or less, about 2 mg or less, about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less, or about 0.01 mg or less of MPLA (total weight per ml liposome suspension). The liposome composition of the adjuvant formulation may have a MPLA:phospholipid mole ratio of about 1:5.6 to about 1:880, or about 1:88 to about 1:220.

In a further aspect, the adjuvant formulation may have a content of saponin (total weight per ml liposome suspension) about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less, or about 0.01 mg or less.

Also provided is an immunogenic composition comprising an immunogen and the adjuvant formulation. The immunogenic composition may typically comprises a physiologically acceptable vehicle. The immunogen of the immunogenic composition can be selected from the group consisting of a naturally-occurring or artificially-created protein, a recombinant protein, a glycoprotein, a peptide, a carbohydrate, a hapten, a whole virus, a bacterium, a protozoan, and a virus-like particle. Preferably, the immunogen of the immunogenic composition may be an HIV-1 envelop protein. A method of immunizing an animal comprising administering the immunogenic composition is also provided.

Further provided is a method of reducing toxicity of a saponin as an adjuvant or preparing an adjuvant formulation comprising adding a monophosphoryl lipid A (MPLA)-containing liposome composition to the saponin, wherein the liposome composition comprises i) a lipid bilayer comprising phospholipids in which the hydrocarbon chains have a melting temperature in water of ≥23° C. and ii) cholesterol at a mole percent concentration of greater than about 50% (mol/mol). The saponin may be selected from the group consisting of QS-7, QS-18, QS-21, and a mixture thereof. Preferably, saponin can be QS-21. The liposome composition may comprise cholesterol at a mole percent concentration of about 55% to about 71% (mol/mol), preferably, about 55% (mol/mol).

BRIEF DESCRIPTION OF THE DRAWING

The accompanying drawings are incorporated into the disclosure and provide non-limiting illustration of various embodiments.

FIG. 5 depicts effect of phospholipid fatty acyl chain length on accessibility of liposomal Chol for binding of QS-21. The experiments were conducted as described in Example 2.

FIG. 8 depicts typical size distributions as measured by light scattering of ALF SUV and ALF MLV in the absence (FIG. 8A) and presence (FIG. 8B) of QS-21 (ALFQ).

DETAILED DESCRIPTION

Figure 1A:
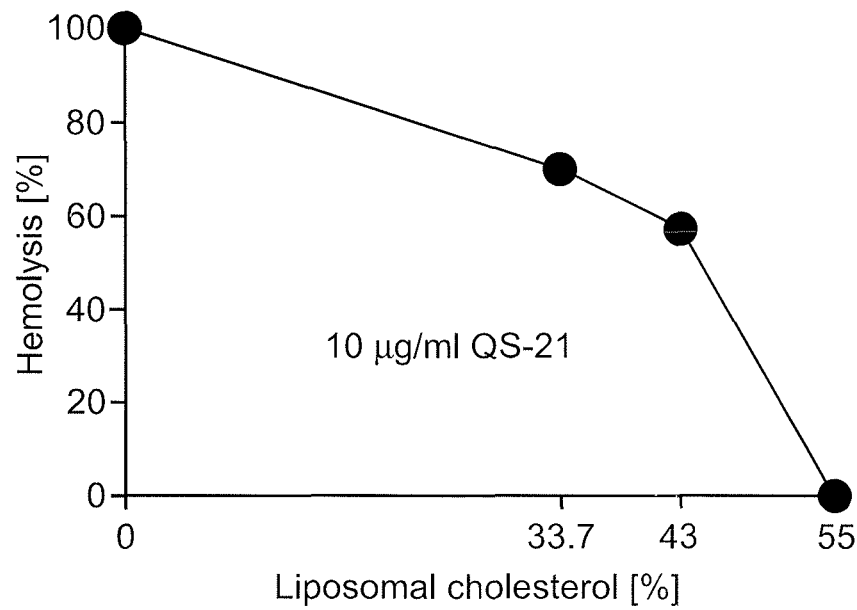
FIG. 1 depicts hemolytic activities of liposome compositions with various QS-21 concentrations (FIG. 1A: 10 μg/ml QS-21.
FIG. 1B: 50 μg/ml QS-21) as described in Example 1.

1. Definitions & Abbreviations
  1.1. Abbreviations and Acronyms
ABTS 2,2'-azino-bis(3-ethylbenzothiazoline-6-sulphonic acid)
ALF Army liposomal formulations
ALFQ ALF plus QS-21
BCIP 5-bromo-4-chloro-3-indolyl-phosphate
Chol cholesterol
cRPMI complete RPMI 1640 medium
DMEM Dulbecco's modified Eagle's medium
DMPC dimyristoyl phosphatidylcholine
DMPG dimyristoyl phosphatidylglycerol
DPPC dipalmitoyl phosphatidylcholine
DSPC distearoyl phosphocholine
ELISA enzyme-linked immunosorbent assay
ELISPOT Enzyme-Linked ImmunoSpot FBS fetal bovine serum
HRP horseradish peroxidase
ID50 50% inhibitory dilution of serum
IFN-γ interferon-γ
IL-4 interleukin-4
L(MPLA) monophosphoryl lipid A (MPLA)-containing liposomes
LAL *Limulus* amebocyte lysate
LPS lipopolysaccharides
MLV multi-lamellar vesicles
MPLA monophosphoryl lipid A
MuLV murine leukemia virus
NBT nitro blue tetrazolium
PBS phosphate-buffered saline
PC phosphatidylcholine
PG phosphatidylglycerol
PHA phytohaemagglutinin
SUV small uni-lamellar vesicles

1.2. Definitions

An "immunogen" is an agent capable of inducing humoral and/or cell-mediated immune response. The immunogen as described herein can be an antigen, a hapten, or an inactivated pathogen. An immunogenic composition as described herein can be, for example, a vaccine formulation.

"Liposomes" as used herein refer to closed bilayer membranes containing an entrapped aqueous volume. Liposomes may also be uni-lamellar vesicles possessing a single membrane bilayer or multi-lamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. Liposomes, as they are ordinarily used, consist of smectic mesophases, and can consist of either phospholipid or non-phospholipid smectic mesophases. Smectic mesophase is most accurately described by Small, HANDBOOK OF LIPID RESEARCH, Vol. 4, Plenum, N.Y., 1986, pp. 49-50. According to Small, "[w]hen a given molecule is heated, instead of melting directly into an isotropic liquid, it may instead pass through intermediate states called mesophases or liquid crystals, characterized by residual order in some directions but by lack of order in others . . . . In general, the molecules of liquid crystals are somewhat longer than they are wide and have a polar or aromatic part somewhere along the length of the molecule. The molecular shape and the polar-polar, or aromatic, interaction permit the molecules to align in partially ordered arrays . . . . These structures characteristically occur in molecules that possess a polar group at one end. Liquid crystals with long-range order in the direction of the long axis of the molecule are called smectic, layered, or lamellar liquid crystals . . . . In the smectic states the molecules may be in single or double layers, normal or tilted to the plane of the layer, and with frozen or melted aliphatic chains."

Lipid A is a set of complex, heavily acylated and amidated diglucosamine diphosphate molecules and is the lipid moiety common to all lipopolysaccharides (LPS; also known as endotoxin) from Gram-negative bacteria. LPS covers virtually the entire outer surface of all Gram-negative bacteria, and lipid A anchors the LPS into the outer lipid surface of the bacterium. The O-polysaccharide portion of LPS in wild-type smooth bacteria is linked to a relatively conserved core oligosaccharide that is expressed in rough mutants, and this in turn is linked to lipid A through highly conserved 2-keto-3-deoxyoctanoic acid sugars that are unique chemical structures sometimes required for bacterial viability and found only in LPS. See, e.g., Alving et al., 2012, *Expert Rev. Vaccines* 11: 733-44. "Monophosphoryl lipid A" is a lipid A congener in which the glucosamine-1-phosphate group on the polar head group has been removed. Numerous congeners of MPLA also exist.

The "mole percent concentration of cholesterol" of a liposome composition as used herein refers to the ratio of Chol:total phospholipid (i.e., phosphatidylcholine and phosphatidylglycerol) originally used in the preparation of the liposome composition.

A "physiologically acceptable vehicle" as used herein refers to a vehicle that is suitable for in vivo administration (e.g., oral, transdermal or parenteral administration) or in vitro use, i.e., cell culture. Exemplary physiologically acceptable vehicles can be those physiologically acceptable constituents of liposomes as disclosed in U.S. Pat. Nos. 4,186,183 and 4,302,459.

"Preferred" and "preferably" as used herein are to be construed for purposes of claim construction in Europe only. The terms should be read out of or omitted from the construction of the sentences and paragraphs in which they appear for purposes of U.S. claim construction.

The term "about" as used herein refers to ±5% of the referenced value.

Unless defined otherwise, all technical and scientific terms used herein have the same meaning as commonly understood by one of ordinary skill in the art. It must be noted that as used herein, the singular forms "a", "and", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

2. Saponin

For the present embodiments, a suitable saponin is Quil A, its derivatives thereof, or any purified component thereof (for example, QS-7, QS-18, QS-21, or a mixture thereof). Quil A is a saponin preparation isolated from the South American tree *Quillaja Saponaria Molina* and was first found to have adjuvant activity. Dalsgaard et al., 1974, *Archiv. für die gesanite Virusforschung*, 44: 243-254. Purified fragments of Quil A have been isolated by HPLC (EP 0 362 278), including, for example, QS-7 and QS-21 (also known as QA7 and QA21, respectively). QS-21 has been shown to induce CD8+ cytotoxic T cells (CTLs), Th1 cells, and a predominant IgG2a antibody response.

3. Monophosphoryl Lipid A (MPLA)-Containing Liposomes (L(MPLA))

Liposomes are closed bilayer membranes containing an entrapped aqueous volume. Liposomes may also be uni-lamellar vesicles possessing a single membrane bilayer or multi-lamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences as described in U.S. Pat. Nos. 6,316,024; 6,126, 966; 6,056,973; and 6,043,094. Liposomes can be made without hydrophilic polymers. Therefore, liposome formulations may or may not contain hydrophilic polymers.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phosphatidylglycerol, phosphatidylinositol, and sphingomyelin as disclosed in U.S. Pat. Nos. 6,056,973 and 5,874,104.

The vesicle-forming lipids may also be glycolipids, cerebrosides, or cationic lipids, such as 1,2-dioleyloxy-3-(trimethylamino)propane (DOTAP); N-[1-(2,3,-ditetradecyloxy)propyl]-N,N-dimethyl-N-hydroxyethylammonium bromide (DMRIE); N-[1(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3 [N—(N',N'-dimethylaminoethane) carbamoyl]cholesterol (DCChol); or dimethyldioctadecylammonium (DDAB) also as disclosed in U.S. Pat. No. 6,056,973. Cholesterol may also be present in the proper range to impart stability to the liposome vesicle, as disclosed in U.S. Pat. Nos. 5,916,588 and 5,874,104. Additional liposomal technologies are described in U.S. Pat. Nos. 6,759,057; 6,406,713; 6,352,716; 6,316,024; 6,294,191; 6,126,966; 6,056,973; 6,043,094; 5,965,156; 5,916,588; 5,874,104; 5,215,680; and 4,684,479. These described liposomes and lipid-coated microbubbles, and methods for their manufacture. Thus, one skilled in the art, considering both the present disclosure and the disclosures of these other patents could produce a liposome for the purposes of the present embodiments. For the present embodiments, the liposome compositions typically contain about 1 mM to about 150 mM phospholipids.

Any of the above exemplary liposomes would include monophosphoryl lipid A (MPLA), or could be combined with other liposomes and lipid A (MPLA). MPLA alone can be toxic to humans and animals. However, when present in liposomes, the toxicity is not detected. See, e.g., Alving et al., 2012. Exemplary procedures for preparation of the liposomes with MPLA as described herein are taught at least in Alving et al., 2012. MPLA serves as a potent adjuvant and serves to raise the immunogenicity of the liposome and peptides, proteins, or haptens associated with the liposome.

For the present embodiments, a typical monophosphoryl lipid A (MPLA)-containing liposome (L(MPLA)) is the one originally referred to as Walter Reed liposomes but now known as Army Liposome Formulation (ALF), as a vaccine adjuvant. See, e.g., Alving et al., 2012. The ALF adjuvant liposomes comprise (1) a lipid bilayer comprising phospholipids in which the hydrocarbon chains have a melting temperature in water of ≥23° C., usually dimyristoyl phosphatidylcholine (DMPC) and dimyristoyl phosphatidylglycerol (DMPG); (2) cholesterol (Chol) as a stabilizer: and (3) monophosphoryl lipid A (MPLA) as an immunostimulator. In human clinical trials, the ALF-type liposomal adjuvant proved to be safe and potent in candidate vaccines to malaria, HIV-1, and cancer. See, e.g., Fries et al., 1992, *Proc. Natl. Acad. Sci. USA*, 89: 358-62; Alving, 2002, *Vaccine*, 20: S56-64. The particular composition of ALF to which QS-21 is added to form ALFQ comprises cholesterol at a mole percent concentration of greater than about 50% (mol/mol), preferably about 55% to about 71% (mol/mol), or more preferably about 55% (mol/mol).

For the present embodiments, an L(MPLA) may comprise a phosphatidylcholine (PC) selected from the group consisting of dimyristoyl phosphatidylcholine (DMPC), dipalmitoyl phosphatidylcholine (DPPC), and disteaiyl phosphatidylcholine (DSPC). The L(MPLA) may also comprise a phosphatidylglycerol (PG) selected from dimyristoyl phosphatidylglycerol (DMPG), dipalmitoyl phosphatidylglycerol (DPPG), and distearyl phosphatidylglycerol (DSPG). The PC to PG ratio (mol/mol) of the liposome may be about 0.5:1, about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1. The liposome may have a content of MPLA (total weight per ml liposome suspension) of about 5 mg or less, about 4 mg or less, about 3 mg or less, about 2 mg or less, about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less, or about 0.01 mg or less. Alternatively, the liposome may have a MPLA:phospholipid mole ratio of about 1:5.6 to about 1:880, preferably about 1:88 to about 1:220. The liposome may comprise multilamellar vesicles (MLV) or small uni-lamellar vesicles (SUV). The small unilamellar vesicles may be about 50 to about 100 nm in diameter, while the multilamellar vesicles may be about 1 to about 4 μm in diameter.

4. Adjuvant Formulations Comprising Liposome and Saponin

An adjuvant formulation known as AS01 (also known as AS01B or AS01E) was previously introduced by GlaxoSmithKline. In AS01, the lipid bilayer was comprised of a neutral lipid that is "non-crystalline" at room temperature, such as dioleoyl phosphatidylcholine, cholesterol, MPLA, and QS-21. See U.S. Published Patent Application No. 2011/0206758. During manufacture of AS01 small unilamellar liposomal vesicles (SUV) are first created and purified QS-21 is then added to the SUV. The QS-21 imparts unique properties in that it binds to the liposomal cholesterol where it causes perforations (holes) or other permanent structural changes in the liposomes. See, e.g., Paepenmuller et al., 2014, *Int. J. Pharm.*, 475: 138-46. A reduced amount of free QS-21 presumably resulted in reduced local injection pain often caused by free QS-21. See, e.g., Waite et al., 2001, *Vaccine*, 19: 3957-67; Mbawuike et al., 2007, *Vaccine*, 25: 3263-69. The AS01B formulation was created " . . . for vaccines where the induction of a yet stronger T-cell-mediated immune response is required." See Garçon et al., 2007, *Expert. Rev. Vaccines*, 6: 723-39. The AS01 formulation is being developed as an adjuvant for a variety of vaccines. See Garcon & Mechelen, 2011, *Expert. Rev. Vaccines*, 10: 471-86. The ASO1 formulation, as described in U.S. Published patent application No. 2011/0206758, may contain cholesterol (sterol) at a mole percent concentration of 1-50% (mol/mol), preferably 20-25% (mol/mol).

As described in the present disclosure, addition of QS-21 to ALF liposomes (resulting in ALF plus QS-21, or "ALFQ") results in complex changes in the membrane biochemistry and physical structure of the liposomal membranes. Factors such as MPLA:phospholipid ratio, and the relative molar concentrations and ratios of QS-21, MPLA, and cholesterol affected the visibility of MPLA and cholesterol. These factors also influence the relative toxicity of added QS-21 as determined by hemolysis of adjacent erythrocytes.

For the present embodiments, the adjuvant formulation comprises monophosphoiyl lipid A (MPLA)-containing liposome composition and at least one saponin, wherein the liposome composition comprises i) a lipid bilayer comprising phospholipids (e.g., dimyristoyl phosphatidylcholine (DMPC) and/or dimyristoyl phosphatidylglycerol (DMPG)) in which the hydrocarbon chains have a melting temperature in water of ≥23° C., and ii) cholesterol at a mole percent concentration of greater than about 50% (mol/mol), or preferably about 55% to about 71% (mol/mol), or more preferably about 55% (mol/mol). At least these two features are distinct from those of AS01 as discussed above. The saponin may be selected from QS-7, QS-18, QS-21, or a mixture thereof, or the saponin preferably may be QS-21. The adjuvant formulation may contain about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less, or about 0.01 mg or less of saponin per ml liposome suspension.

The adjuvant formulations of the present embodiments may be used to mix with an immunogen to obtain an immunogenic composition, for example, a vaccine formulation. The immunogenic composition may comprise a physiologically acceptable vehicle, for example, any one of those described in U.S. Pat. No. 5,888,519. The immunogenic composition may comprise naturally-occurring or artificially-created proteins, recombinant proteins, glycoproteins, peptides, carbohydrates, haptens, whole viruses, bacteria, protozoa, or virus-like particles as the immunogen. The immunogenic composition may be a HIV-1 envelop protein, e.g., gp140. The immunogenic formulation may be suitably used as a vaccine for influenza, HIV-1, Hepatitis A, Hepatitis B, Human Papilloma virus, Meningococcal type A meningitis, Meningococcal type B meningitis, Meningococcal type C meningitis, Tetanus, Diphtheria, Pertussis, Polio, *Haemophilus influenza* type B, Dengue, Hand Foot and Mouth Disease, Typhoid, Pneumococcus, Japanese encephalitis virus, Anthrax, Shingles, Malaria, Norovirus, or cancer.

EXAMPLES

The following examples are provided in order to demonstrate and further illustrate certain representative embodiments and aspect of the present disclosure and are not to be construed as limiting the scope of the specification or claims.

Materials and Methods

Lipids, Saponins, and Other Reagents

Dimyristoyl phosphatidylcholine (DMPC), dimyristoyl phosphatidylglycerol (DMPG), and synthetic monophosphoryl lipid A (MPLA) (PHAD™), were purchased from Avanti Polar Lipids (Alabaster, Ala., USA). DMPC and Chol were dissolved in freshly distilled chloroform, and DMPG and MPLA were dissolved in chloroform:methanol (9:1). Purified QS-21 (Desert King International San Diego, Calif., USA) was dissolved in PBS at 1 mg/ml. Saponin was purchased from Sigma-Aldrich (St. Louis, Mo., USA).

Horseradish peroxidase (HRP)-linked-sheep anti-mouse IgG HRP was purchased from The Binding Site (cat. no. AP272). HRP-linked goat anti-mouse IgG1 (A90-105P), HRP-link goat anti-mouse IgG2a (A90-107P), HRP-linked goat anti-mouse IgG2b (A90-109P), HRP-linked goat anti-mouse IgG3(A90-111P), and purified mouse IgG1 (MI10-102), IgG2a (MI10-103), IgG2b (MI10-104), and IgG3 (MI10-105) were purchased from Bethyl Laboratories (Montgomery, Tex., USA). Uncongugated goat anti-mouse IgG Fab (1015-01) was from Southern Biotech (Birmingham, Ala., USA). Purified anti-mouse IFN-γ (51-2525KZ), purified rat anti-mouse IL-4 (BVD4-1D11), biotin-labeled anti-mouse IFN-γ (51-1818KA), and biotin-labeled rat anti-mouse IL-4 (BVD6-24G2) were purchased from BD Biosciences (Franklin Lakes, N.J., USA).

Dulbecco's modified Eagle's medium (DMEM) containing 10% fetal bovine serum (FBS), 100 unit/ml penicillin, 100 μg/ml streptomycin, and 2 mM L-glutamine was used for culturing TZM.bl cells and for HIV-1 neutralization assays. Complete RPMI 1640 medium (cRPMI) containing with 10% FBS, 100 unit/ml penicillin, 100 μg/ml streptomycin, and 2 mM L-glutamine, was used for culturing mouse splenic lymphocytes and for ELISPOT analyses.

Preparation of Liposomes

Liposomes were prepared as previously described in Matyas et al., 2003, Methods Enzymol., 373: 34-50. For Examples 1-3, lipids were mixed, dried under vacuum, and then liposomes were formed in PBS, pH: 7.4, in a final concentration of either 50 mM or 1.272 mM of total phospholipids. Liposomal phosphatidylcholine and phosphatidylglycerol were in a molar ratio of 9:1. Liposomal Chol varied as indicated. When MPLA was used the molar ratio of MPLA:total phospholipid was 45:1, or 5.6:1 where indicated. The mole percent concentrations of liposomal Chol are based on the ratio of Chol:total phospholipid (i.e., phosphatidylcholine and phosphatidylglycerol) originally used in the preparation of the liposomes.

To evaluate adjuvant potency, Army liposome formulations (ALF) containing DMPC, DMPG, Chol, and MPLA were prepared by the lipid deposition method as described in Matyas et al., 2003. For Example 4, lipids were mixed and dried by rotary evaporation. Multi-lamellar vesicles (MLV) were formed by adding PBS, pH 7.4, at a final concentration of either 50 mM, or 20 mM, or 2 mM of total phospholipids in the aqueous liposome suspension. A total of 20 μg of MPLA was used for each liposome preparation, and the molar ratios between MPLA and phospholipids were 1:220, 1:88, and 1:5.6, respectively. Liposomal phosphatidylcholine and phosphatidylglycerol were in a molar ratio of 9:1. Liposomal Chol concentration was 43 mol % in all ALF preparations lacking QS-21. Liposomes were microfluidized using a Microfluidics LV1 low volume high shear microfluidizer (ATS Scientific Inc., Burlington, Ontario, Canada) at 30,000 psi to form SUVs. The diameter size distributions of liposomes were measured by Horiba LB-550 particle sizer (Horiba Scientific, New Jersey, N.J.). Army liposome formulations plus QS-21 (ALFQ) were made by mixing MLV or SUV liposomes in which the Chol concentration was 55 mol % with QS-21. The QS-21 irreversibly binds to the Chol in the liposomes under these conditions with no detectable free QS-21 present in the buffer. The total amount of QS-21 in each ALFQ formulation used for immunization was 10 μg.

A total injection dose of 10 μg of HIV-1 clade C CN54 gp140 envelope antigen (Polymun Scientific Inc., Klosterneuberg, Austria) was mixed with each formulations of ALF or ALFQ liposomes in PBS. Four different ALF-gp140 formulations were made, having liposomal MPLA:phospholipid ratios of 1:220 or 1:88 for MLV, and 1:88 or 1:5.6 for SUV. Three different ALFQ-gp140 formulations were prepared by adding QS-21 to ALF SUV or MLV, with the MLV having MPLA:phospholipid ratios of either 1:220 or 1:88 and the ALF SUV 1:5.6.

Cholesterol Analysis

Cholesterol content was analyzed to confirm the cholesterol, and indirectly, the phospholipid concentration of the liposome formulations by the established methods. See, e.g., Zlatkis et al., 1953, *J. Lab. Clin. Med.*, 41: 486-492. Briefly, 5 to 200 µl of liposomes were added to water to a final volume of 200 µl. Three ml of glacial acetic acid were added, followed by the addition of 2 ml of 0.1% ferric chloride in glacial sulfuric acid. After mixing and then equilibrating, the samples to mom temperature, absorbance was read at 560 nm. The cholesterol concentration of the liposomes was determined from a cholesterol standard curve.

Hemolytic Assay

Hemolysis of red blood cells was used as a measure both of the relative amount of free QS-21, and of the toxicity of QS-21 under the indicated experimental conditions. Human red blood cells were purchased from the Research Blood Components LLC (Boston, Mass., USA) under a Walter Reed Army institute of Research protocol reviewed by the independent Institutional Review Board, Division of Human Subjects. Erythrocytes were washed with PBS and were quantified by a Beckman Coulter counter model ACT10 (Indianapolis Ind., USA). In each assay of this study, hemolytic activity of QS-21 incubated with or without liposomes was determined in 220 µl volume and each step of the assay was performed at room temperature (22° C.). One hundred microliters of QS-21 dilution was incubated with 100 µl of liposomes, or PBS only, on a Daigger Rocker (Vernon Hills, Ill., USA) for 15 minutes. After mixing the liposomes, $2\times10^7$ erythrocytes in 20 µl of PBS were added to the mixture and incubated on a Daigger Rocker for an additional 30 minutes. Plates were centrifuged at 800×g for 6 min. Supernatant was transferred to a polystyrene 96-well plate, and absorbance was read at 541 nm. Hemolysis by QS-21 binding to liposomal Chol was expressed as % of maximum hemolysis by free QS-21.

*Limulus* Amebocyte Lysate Assay

*Limulus* amebocyte lysate (LAL) assay was used as a probe to examine the roles of phospholipid chain length and mole fraction of Chol on the liposomal surface expression of MPLA. A lysate of amebocytes from the blood of *Limulus polyphemus* (Atlantic horseshoe crab) containing a clotting protein is widely used as a surrogate probe for detecting the endotoxic activity of LPS or lipid A. See, e.g., Brandenburg et al., 2009, *Curr. Med. Chem.*, 16: 2653-2660. Although the exact molecular epitope or structure of lipid A (or MPLA) to which the *Limulus* protein binds is still not entirely clear, incorporation of lipid A into the liposomal bilayer greatly masks both the endotoxic and the LAL activities. See, e.g., Harmon et al., 1997, *Anal. Biochem.*, 250: 139-146. It is believed that masking of the LAL activity is due to sequestration of the "*Limulus*-reactive" group of lipid A in the liposomal lipid bilayer resulting in inhibition of binding of the *Limulus* protein to the lipid A. However, "*Limulus*-positive" (i.e., reactive) and "*Limulus*-negative" (non-reactive) liposomes can be created by varying the concentration of liposomal lipid A to higher or lower amounts, respectively. See Richardson et al., 1983, *Infect. Immun.*, 39: 1385-1391. As with other liposomal lipids, lipid A can self-associate to form lipid A-enriched domains, and these may be lamellar or non-lamellar. See, e.g., Kubiak et al., 2011, *Biophys. J.*, 100: 978-986; Brandenburg et al., 1998, *Chem. Phys. Lipids,* 91: 53-69. High concentrations of liposomal lipid A presumably lead to self-association or phase separation, with increased surface visibility of the *Limulus*-reactive group of lipid A.

*Limulus* amebocyte lysate (LAL) Kinetic-QCL assay was purchased from Lonza (Allendale, N.J., USA). The assay was performed on the Spectramax M5 (Molecular Devices) platform using the SoftMax Pro Chromo-LAL protocol at 37° C., using the following parameters: $\Delta t=150$ seconds, measurement filter=405 nm, $\Delta OD=0.2$, number of reads=40. The results were presented in EU/ml units.

Immunization of Mice

Female Balb/c mice (Charles River Laboratories, Indianapolis, Ind., USA) (5-6 weeks of age; 6/group) were immunized intramuscularly (IM) with 0.05 ml of the vaccines by injection in alternative rear thighs at 0, 3 and 6 weeks. Four mouse groups were immunized with the ALF+gp140 formulations listed above and three groups were immunized with the ALFQ+gp140 formulations. One mouse group was not immunized, and was used as negative control for the immunological studies. The animals were bled prior to the first immunization and 3 and 6 weeks after the primary immunization. At week 9, the animals were terminally bled and the spleens were collected.

Detection of Antibody Responses after Vaccination by ELISA

To determine endpoint titers of IgG antibodies, gp140 protein (0.1 µg/0.1 ml/well in PBS) was added to Immulon 2HB flat bottom plates (Thermo Fisher Scientific, Waltham, Mass., USA). After incubating overnight at 4° C., all further steps were performed at room temperature. Plates were blocked with 250 µl of 0.5% milk/0.1% Tween 20 in PBS (blocking buffer) for 2 h. Samples were serially diluted two fold starting with 1:400 dilution, and 100 µl of diluted serum samples were added to the plate. Plates were incubated for 1 hour and washed 4 times with Tris-buffered saline/0.1% Tween 20. HRP-linked sheep anti-mouse IgG (0.1 µg in 100 µl blocking buffer) was added to each well and plates were incubated for 1 hour followed by washing. One hundred µl of ABTS 2-component substrate (Kirkegaard and Perry Laboratories, Gaithersburg, Md., USA) were added to each well, and plates were incubated for 1 hour. Color development was stopped by adding 100 µl/well of 1% SDS. The absorbance was read at 405 nm. End point titer was defined as the dilution at which the absorbance was twice background.

IgG subtype determination was modified from Glenn et al., 1995, *Immunol. Let.* 47: 73-78. A standard curve was made by using unconjugated goat anti-mouse IgG (Fab). One hundred µl of Fab (1 µg/ml in PBS) was added to the wells of 96-well Immulon 2HB flat bottom plates and the plates were incubated overnight at 4° C. Plates were washed 3 times with 0.05% Tween 20 in PBS (washing buffer), blocked with 250 µl/well of 0.5% skim milk in PBS (blocking buffer), and incubated at room temperature (RT) for 1 hour. After washing, 100 µl of blocking buffer were added to each well. Purified mouse IgG1, IgG2a, IgG2b, and IgG3 were diluted two-fold starting from 200 ng/ml of blocking buffer. One hundred µl of each dilution were added to the plates. Plates were incubated at room temperature for 2 hours, and washed 3 times. One hundred µl of HRP-linked goat anti-mouse IgG1, IgG2a, IgG2b, and IgG3 (1:1000 dilution in blocking buffer) were added to the corresponding wells, and plates were incubated at room temperature for 1 hour. Plates were washed and 100 µl of ABTS were added. Color development was stopped with 100 µl/well of 1% SDS. Absorbance was read at 405 nm. For subclass analysis, pooled mouse serum in each group was added to gp140 coated plates as for the standard ELISA. HRP-linked goat anti-mouse IgG1, IgG2a, IgG2b, and IgG3 were added and the ELISA was conducted together with the standard curve.

The concentration of the immunoglobulin subclasses of the pooled sera of each group was calculated using the standard curve.

Enzyme-Linked ImmunoSpot Assays for INF-γ and IL-4

Spleens from euthanized mice, were pressed through a 100-μm nylon cell strainer (Thomas Scientific, Swedesboro, N.J., USA, cat No. 4620F05) with the plunger of a syringe. Splenic cell suspensions were collected in and washed 3 times with cRPMI medium. ELISPOT was conducted as described in Rao et al., 2002, *J. Virol.*, 76: 9176-85. Prior to the harvesting of spleens, multiScreen 96-well microtiter plates (EMD Millipore, Billerica, Mass., USA) were pre-treated with 70% ethanol, washed 3 times with PBS and coated with 100 μl/well of either 5 μg/ml of capture INF-γ-specific IgG diluted in PBS or 2 μg/ml of capture IL-4-specific specific IgG diluted in PBS. Plates were incubated overnight at 4° C., then washed 2 times with cRPMI and blocked with 200 μl/well cRMPI at RT for 2 hours. Fifty μl of mouse cell suspensions ($8\times10^6$ cells/ml) were plated in duplicate for each cytokine assay. Either 50 μl of cRPMI for unstimulated cells, or 10 μg/ml gp140 CN54 for stimulated cells, or with 50 μl of 10 μg/ml Con-A as a positive control, or 50 μl of 2 μg/ml PHA as negative control were added to corresponding wells. Plates were incubated for 18 hours at 37° C. in a CO2 incubator. Plates were washed 3 times with PBS containing 0.002% Tween 20 (washing buffer). One hundred μl of 2 μg/ml biotin-labeled detection INF-γ or IL-4 antibodies in PBS were added to each well. Plates were incubated at room temperature for 3 hours and then washed 3 times. One hundred μl of streptavidin-alkaline phosphatase solution (Southern Biotech, cat. No. 7100-04) diluted 1:1000 in PBS/5% FCS/0.001% Tween) were added to each well, and plates were incubated at room temperature for 1 hour in dark. Plates were washed 3 times and 100 μl/well of BCIP/NBT chromogen substrate (Kirkegaard & Perry, cat. No. 50-81-07) were added. After spots developed, plates were thoroughly rinsed with distilled water. Frequencies of IFN-γ and IL-4-producing cells were measured using a BioReader 3000 Elispot Reader (Bio-Sys GmbH, Karben, Germany). Data are expressed as the mean number of spots.

Neutralization Assay

Neutralizing antibody responses against two tier 1 HIV-1 Env pseudoviruses were measured by using luciferase-based virus neutralization assays with TZM.b1 cells as previously described. See, e.g., Brown et al., 2007, *J. Virol.*, 81: 2087-91. The 50% inhibitory dilution of serum (ID50) was calculated as the serum dilution that resulted in a 50% reduction in relative luminescence units compared with the virus control wells after the subtraction of cell control relative luminescence units. Briefly, 4-fold serial dilutions of serum samples in 25 μl were assayed in a 96-well flat-bottom plate in duplicate in 10% Dulbecco's modified Eagle's medium (DMEM). HIV clade C, GS015 PV and MW965.26 PV (25 μl) were added to each well and the plates were incubated for 1 h at 37° C. TZM.b1 cells were then added (104 cells/well) in a 50 μl volume in 10% DMEM containing DEAE-dextran, and neutralizing antibody titers were determined as previously described in Brown et al., 2008. Murine leukemia virus (MuLV) negative controls were included in all assays.

Statistical Analysis

Statistical analysis was performed using GraphPad Prism. For antibody subtype quantification, sigmoidal 4-parameter nonlinear regression curve fit was used. Statistical comparison between multiple groups was performed using one-way ANOVA, Kruskal-Wallis test with Dunn's correction. Column comparison analyses were performed using unpaired t-test (Mann Whitney test).

Example 1—Characterization of the Effect of Liposomal Chol on Hemolytic Activity of Co-Incubated QS-21

Figure 1B:
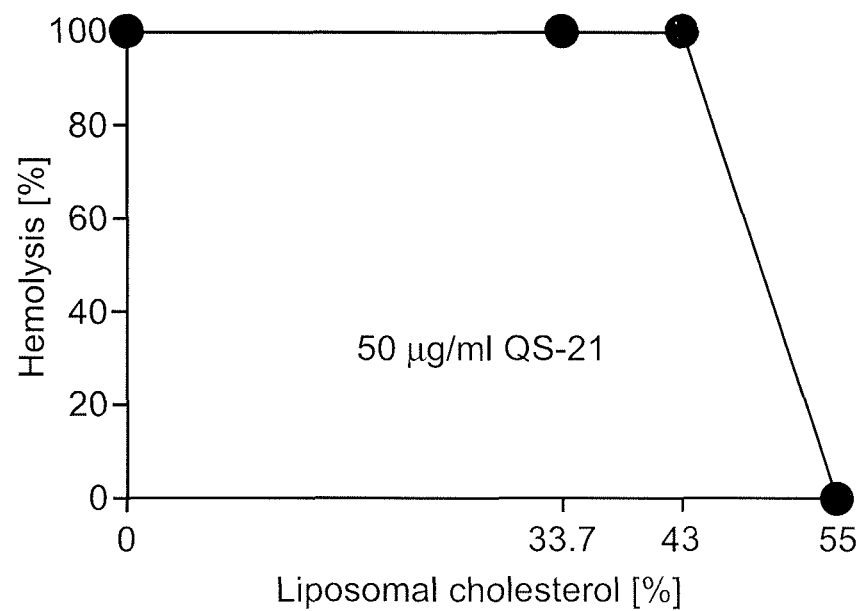

The hemolytic activities of liposome compositions with QS-21 were characterized first by varying QS-21 concentration. Briefly, fifty millimolar phospholipid liposomes containing 33.7%, 43%, and 55% cholesterol were mixed and incubated with 10 μg/ml and 50 μg/ml QS-21 at room temperature for 20 minutes. Red blood cells were added to the mixture of liposome-QS-21, and incubated for 30 minutes. Free QS-21 served as positive control. Cells were centrifuged and the optical density of supernatant was measured at 541 nm to reflect the levels of hemolysis. The results, as presented in FIG. 1, suggest that the levels of hemolysis by liposome compositions with QS-21 depends upon the concentration of cholesterol in the liposomes.

Figure 2:
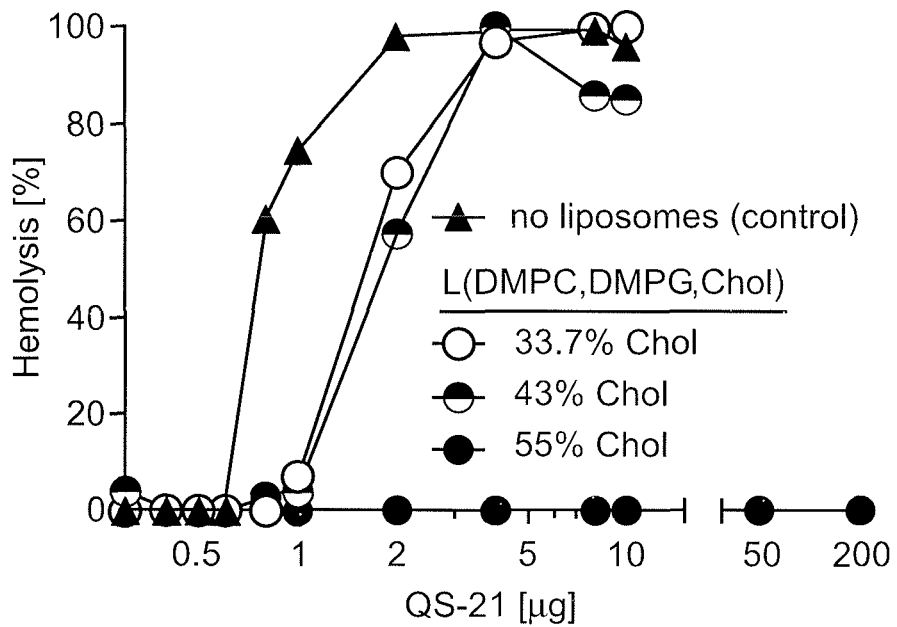
FIG. 2 depicts hemolysis of erythrocytes by QS-21 pre-incubated with liposomes as described in Example 1. QS-21 was mixed with DMPC/DMPG liposomes containing a total of 5 μmol of phospholipids at 22° C. The liposomes also contained 33.7, 43, or 55 mol % Chol.
Figure 3:
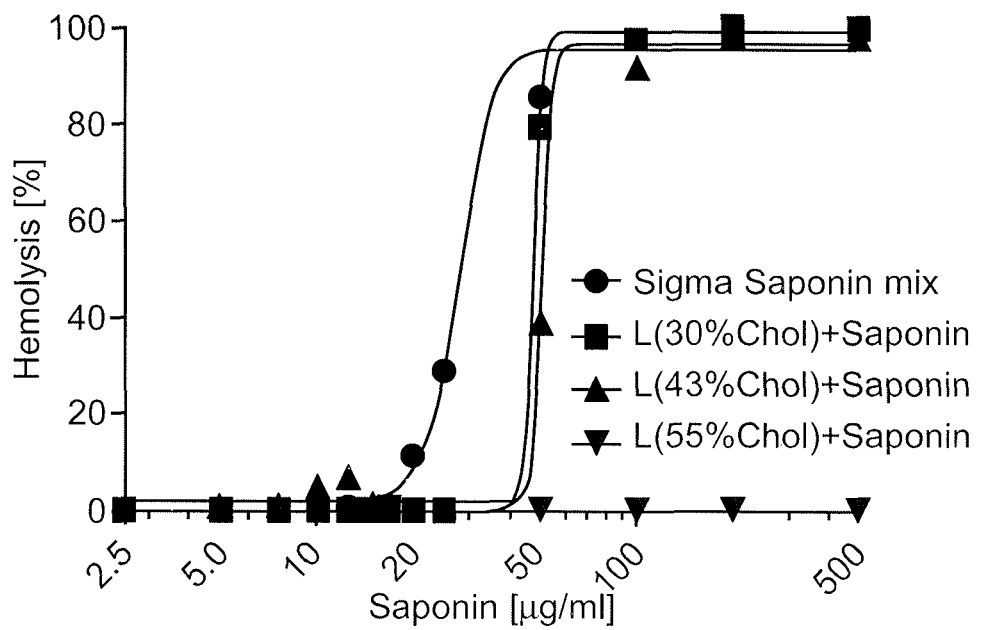
FIG. 3 depicts hemolysis of erythrocytes by saponin pre-incubated with liposomes as described in Example 1.

The hemolytic activities of liposome compositions with QS-21 were further characterized by varying mol % of liposomal Chol. The degree of erythrocyte damage caused by QS-21 was found to be inversely related to the mol % of liposomal Chol that had been pre-incubated with QS-21 (FIG. 2). While free QS-21 caused maximum hemolysis at approximately 2 μg, maximum hemolysis occurred at approximately 4 μg of QS-21 when QS-21 was pre-incubated with liposomes containing either 33.7 or 43 mol % Chol (FIG. 2). Liposomes having 55 mol % Chol completely blocked the hemolytic effect of QS-21 up to 200 μg (FIG. 2). Similar results were observed for liposome compositions containing varying concentrations of saponin (FIG. 3). No hemolysis with up to 500 μg/ml saponins was detected when liposomes contained 55 mol % cholesterol.

Example 2—Characterization of Interaction Between QS-21 and Liposomal Chol

Figure 4:
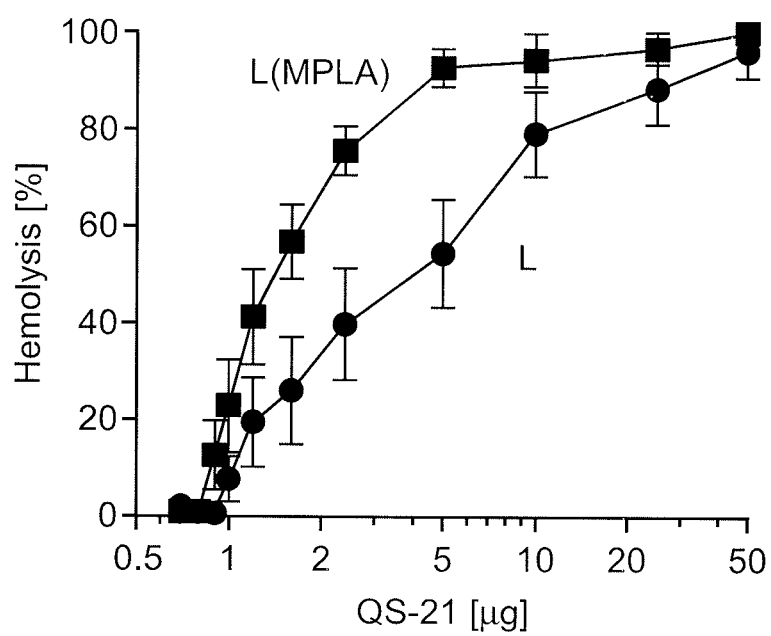
FIG. 4 depicts inhibition of binding of QS-21 to liposomal Chol by liposomal MPLA. The experiments were conducted as described in Example 2. The mean±S.D. is shown with 14 independent liposome batches of L, and with 4 independent batches of L(MPLA).

Binding of QS-21 to DMPC/DMPG/Chol liposomes containing 0.127 μmol total phospholipids and 50 mol % Chol was compared to the same liposomes that also contained 0.025 μmol of MPLA (DMPC/DMPG/Chol/MPLA). Briefly, QS-21 was pre-incubated with liposomes consisting of a total of 0.127 μmol of phospholipid (DMPC/DMPG, 9/1), 50 mol % Chol, and either lacking or containing MPLA, (L) or L(MPLA) (MPLA:phospholipid=1:5.6). Then the hemolytic activities were measured. As shown in FIG. 4, 50 mol % Chol liposomes without MPLA (L) reached 100% hemolysis only at the concentration of 25 μg of QS-21. With liposomes having MPLA (L(MPLA)), hemolysis reached a maximum level at 5 μg of QS-21, which was similar to the hemolytic curve of free QS-21. It is thus clear that 50% Chol was less visible to QS-21 in liposomes containing MPLA when compared to those lacking MPLA.

Figure 5A:
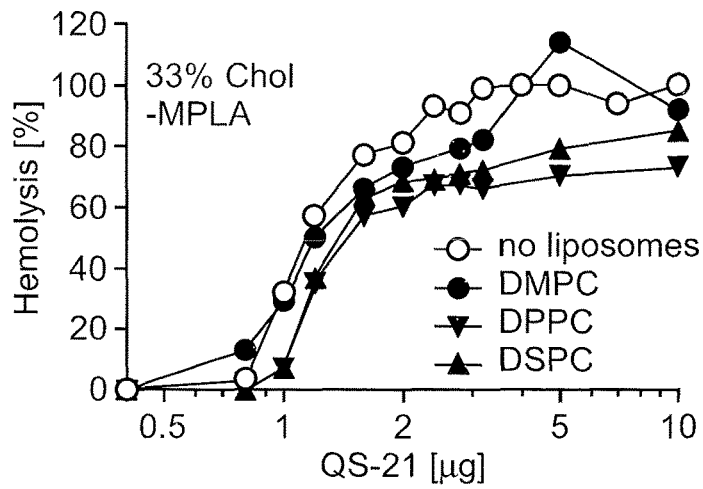
FIG. 5A illustrates the results of the liposomes with 33.7 mol % Chol and no MPLA.
Figure 5B:
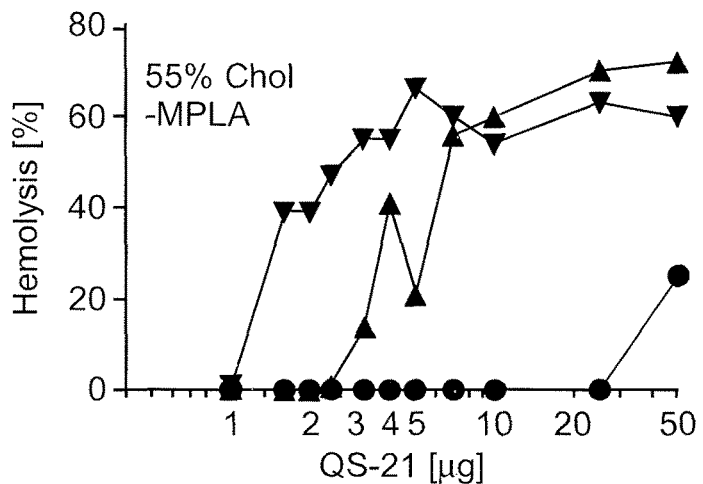
FIG. 5B illustrates the results of the liposomes with 55 mol % Chol, and no MPLA.
Figure 5C:
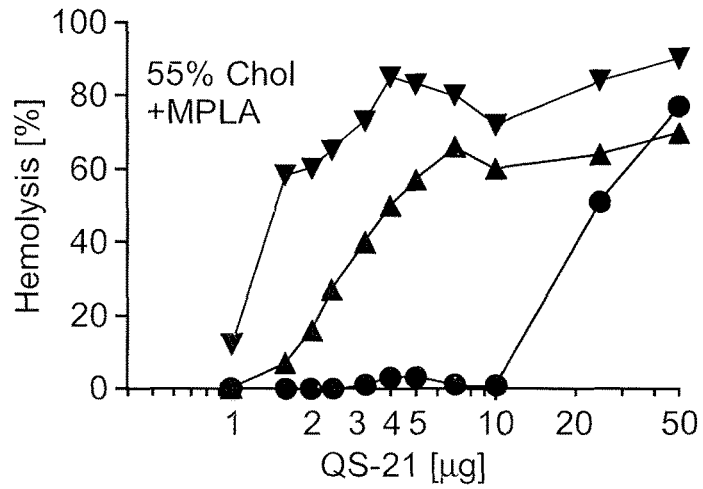
FIG. 5C illustrates the results of the liposomes with 55 mol % Chol and MPLA.

Three liposome compositions containing 0.114 μmol of phosphatidylcholine, consisting of DMPC, DPPC, and DSPC, respectively, together with 0.0127 μmol of DMPG, and containing either 33.7% or 55% Chol with or without 2.85 nmol MPLA, were pre-incubated with QS-21 (FIG. 5). Then the hemolytic activities were evaluated. As shown in FIG. 5A, with up to 10 μg of QS-21, little or none of the QS-21 bound to DMPC, DPPC, or DSPC liposomes having 33.7 mol % Chol. However, increasing the liposomal Chol to 55% (FIG. 5B) increased the binding of QS-21 to Chol in DSPC liposomes, and notably in DMPC liposomes. In contrast, DPPC liposomes with 55% Chol bound much less QS-21 than the DMPC or DSPC liposomes (FIG. 5B). The presence of MPLA inhibited the binding of QS-21 to DMPC liposomes with 55% Chol, but did not inhibit the binding to either DPPC or DSPC liposomes (FIG. 5C).

Figure 6A:
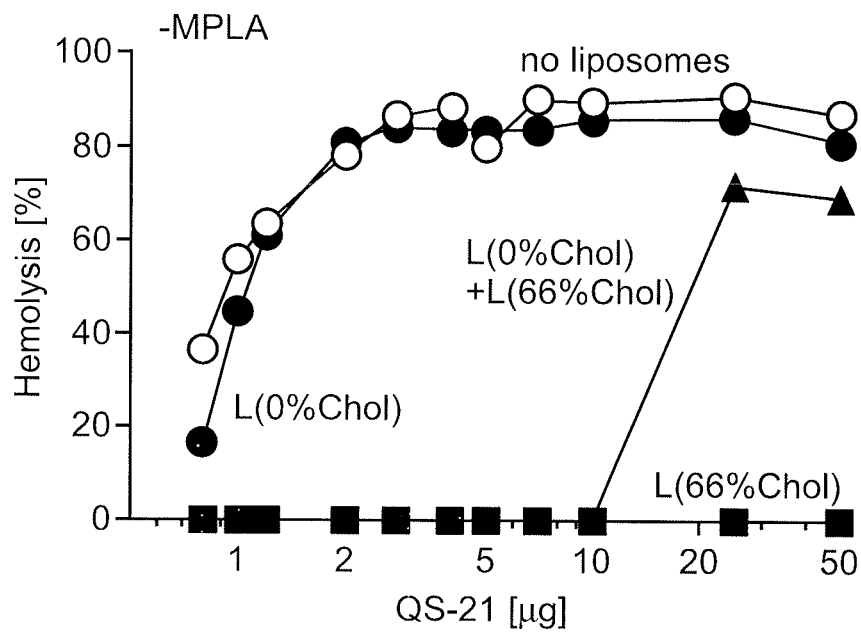
FIG. 6 depicts inhibition of Chol transfer between DMPC/DMPG liposomes by MPLA. Chol transfer was detected by QS-21 binding to liposomes containing either: no MPLA (FIG. 6A) or MPLA (MPLA:phospholipid=1:5.6) (FIG. 6B).
Figure 6B:
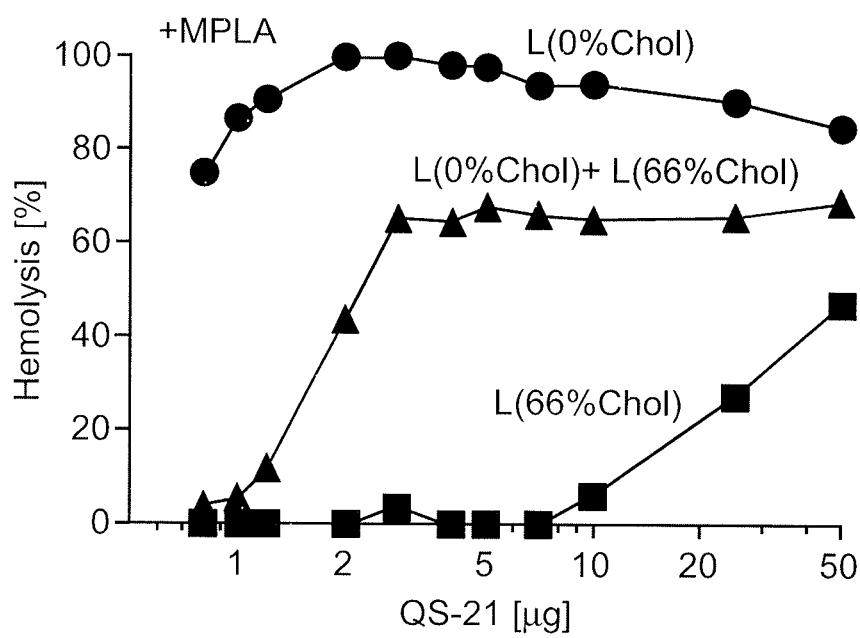

Furthermore, Chol transfer from liposomes containing 66% Chol to liposomes lacking Chol was detected by using QS-21 as a probe (FIG. 6). Preincubation of QS-21 with [L(0% Chol)+L(66% Chol)] resulted in hemolytic activity of QS-21 that was intermediate between that observed after preincubation of QS-21 separately with either L(0% Chol) or L(66% Chol) (FIG. 6A). Preincubation of QS-21 with an equal mixture of liposomes containing MPLA, and containing or lacking Chol [L(0% Chol+MPLA)+L(66% Chol+MPLA)] also resulted in an intermediate level of hemolysis due to QS-21 (FIG. 6B). However, the curve of [L(0% Chol+MPLA)+L(66% Chol+MPLA)] shown in FIG. 6B was shifted toward greater hemolytic activity when compared with liposomes lacking MPLA [L(0% Chol)+L(66% Chol)] (FIG. 6A). It is thus clear that the presence of MPLA in liposomes either inhibited the Chol transfer between liposomes or shielded the visibility of the Chol in the mixture of liposomes.

Example 3—Suppression of *Limulus* Amebocyte Lysate Recognition of DMPC/DMPG/Chol/MPLA Liposomes by Increasing Amount of Liposomal Chol

Figure 7A:
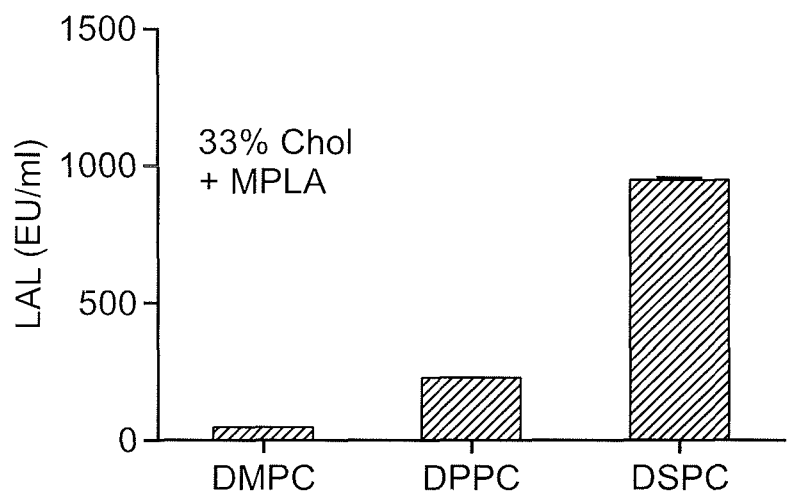
FIG. 7 depicts suppression of LAL positivity of DMPC/DMPG/Chol/MPLA liposome by increasing liposomal Chol contents. Results of LAL binding to liposomes containing 33.7 mol % Chol are shown in FIG. 7A, while results of LAL binding to liposomes containing 55 mol % Chol are shown in FIG. 7B.
Figure 7B:
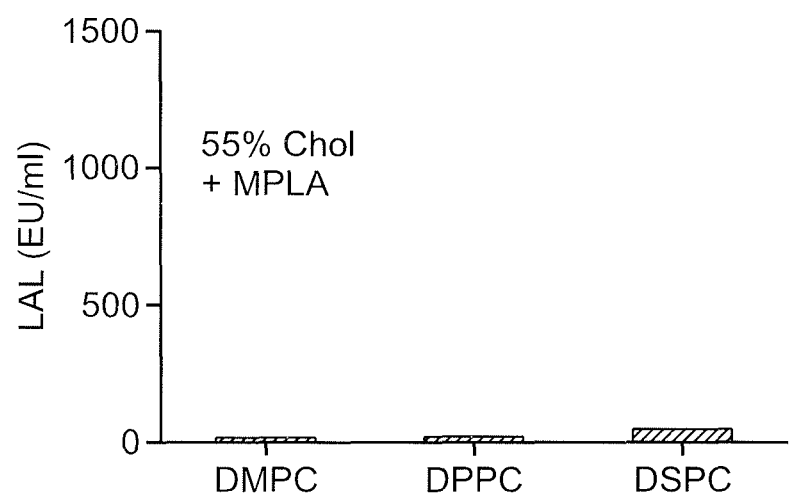

*Limulus* amebocyte lysate (LAL) assay was conducted for DMPC/DMPG/Chol/MPLA liposomes containing various amounts of Chol. FIG. 7A shows that the MPLA in DMPC/DMPC/Chol/MPLA, DPPC/DMPC/Chol/MPLA, or DSPC/DMPC/Chol/MPLA liposomes containing 33.7 mol % Chol was detected by the LAL assay. The recognition of MPLA by LAL in liposomes containing 33.7% Chol was proportional to the length of saturated fatty acyl chains of phosphatidylcholine, with LAL binding in the order DSPC>DPPC>DMPC. However, at 55 mol % Chol the ability of LAL to detect MPLA in each of the liposomes was dramatically reduced (FIG. 7B).

Figure 8A:
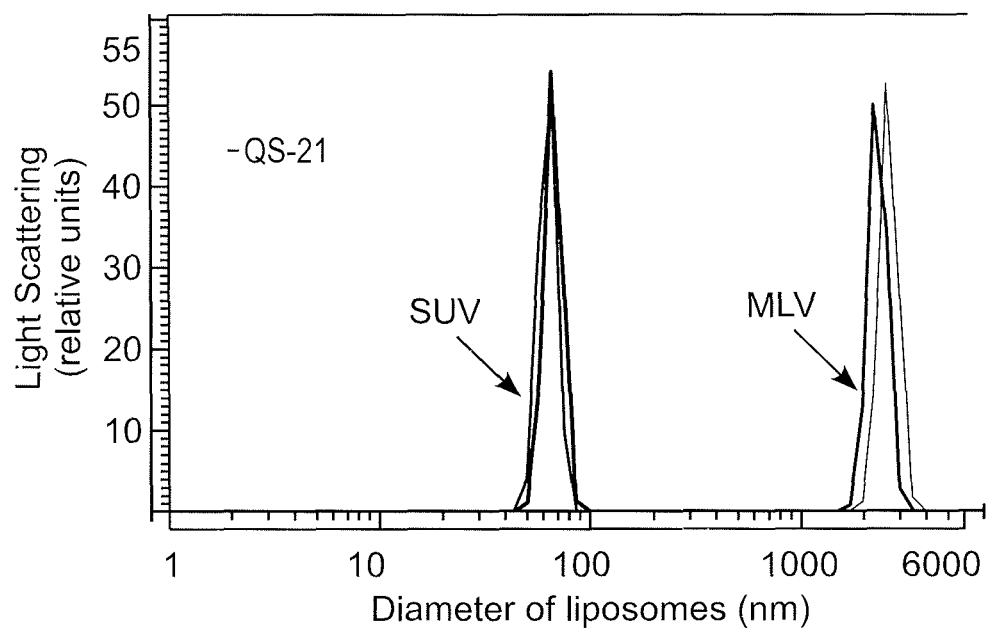
In FIG. 8A, the two SUV curves comprised liposomes having MPLA:phospholipid ratios of 1:88 or 1:5.6. The two MLV curves comprised (from left to right): liposomes having MPLA:phospholipid ratios of 1:220 or 1:88.
Figure 8B:
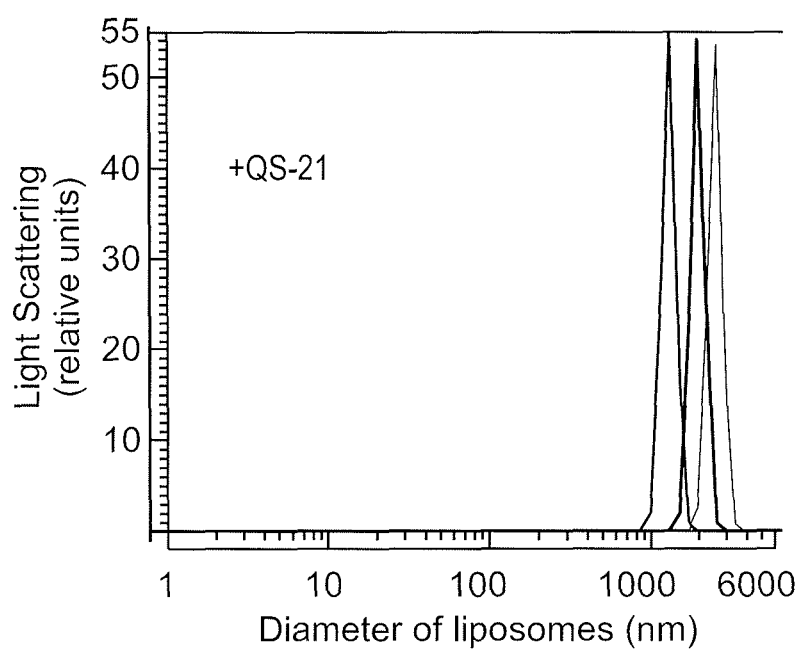
In FIG. 8B, the curves represent ALFQ in which the initial ALF comprised (from left to right): MLV with MPLA:phospholipid ratio of 1:220; and SUV with MPLA:phospholipid ratios of 1:88 and 1:5.6, respectively.

Example 4—Characterization of Adjuvant Potency of Formulations Comprising L(MPLA) and Saponin To test the effects of liposome size on adjuvant potency, large MLV and SUV, each being a type of ALF liposomes (i.e., containing MPLA), were constructed. As shown in FIG. 8, based on light scattering analysis the diameter size range of the ALF SUV particles was between 50 and 100 nm, and ALF MLV was between 1 and 4 μm. Although this latter result with MLV indicates that light scattering analysis detected many large particles, MLV also contains numerous small particles in a hyperbolic distribution as shown by electronic particle size analysis. See, e.g., Alving et al., 1975, *Biochim. Biophys. Acta.,* 394: 157-65. Thus, with light scattering analysis the small particles that were present in the MLV were overshadowed by the large particles. In any case, each measured particle population was narrow and had only one median peak. In the case of ALF SUV this indicated the presence of a homogenous population. Even at a high MPLA:phospholipid ratio ALF SUV formed a single distribution of small particles. However, in contrast to liposomes lacking QS-21, the median size of all ALF liposomes containing QS-21 (ALFQ), regardless of whether the initial ALF particles were SUV or MLV, were measured in the micrometer range (FIG. 8B). As indicated above, this does not exclude the possibility of concurrent populations of small particles. Within the overall size range of ALFQ particles distinct individual subpopulations of large ALFQ having slightly different median sizes occurred depending on the MPLA:phospholipid ratio (FIG. 8B).

Figure 9A:
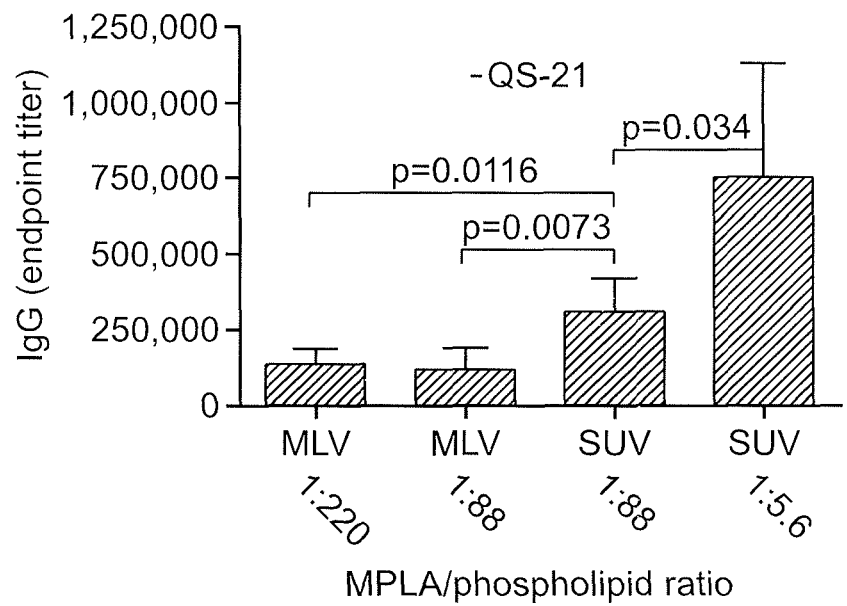
FIG. 9 depicts IgG endpoint titers to gp140. Mice were immunized with ALF+CN gp140 (FIG. 9A) and ALFQ+CN gp140 (FIG. 9B) containing the indicated MPLA:phospholipid molar ratios in which 20 μg of MPLA was present in each formulation. Sera were from week 9 and were assayed by ELISA. Values are the mean of 6 animals/group±standard deviation.
Figure 9B:
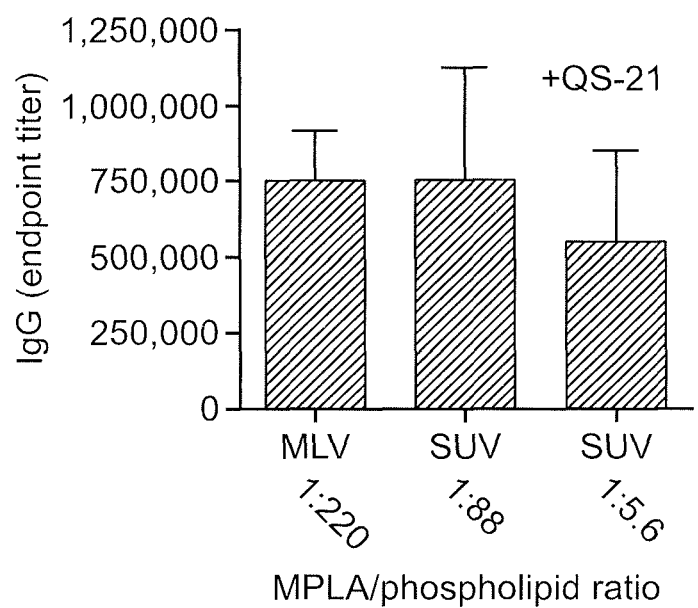

Antibody production was measured from immunized mice using various compositions as described in Materials and Methods, and the results were compiled in FIG. 9. As shown in FIG. 9A, ALF SUV containing MPLA:phospholipid in the ratio of 1:88 induced higher IgG anti-gp140 binding antibody production in mice than ALF MLV having the same MPLA:phospholipid ratio in a statistically significant fashion. ALF SUV with an MPLA:phospholipid ratio of 1:5.6 induced the highest titer of binding antibodies. FIG. 9B shows that all ALFQ-adjuvanted formulations induced significantly higher binding antibodies to gp140 than any of the ALF MLV-adjuvanted formulations. The total gp140-specific IgG binding antibody levels in all ALFQ-adjuvanted groups appeared independent of the size of the liposomes or the relative phospholipid concentration.

Figure 10A:
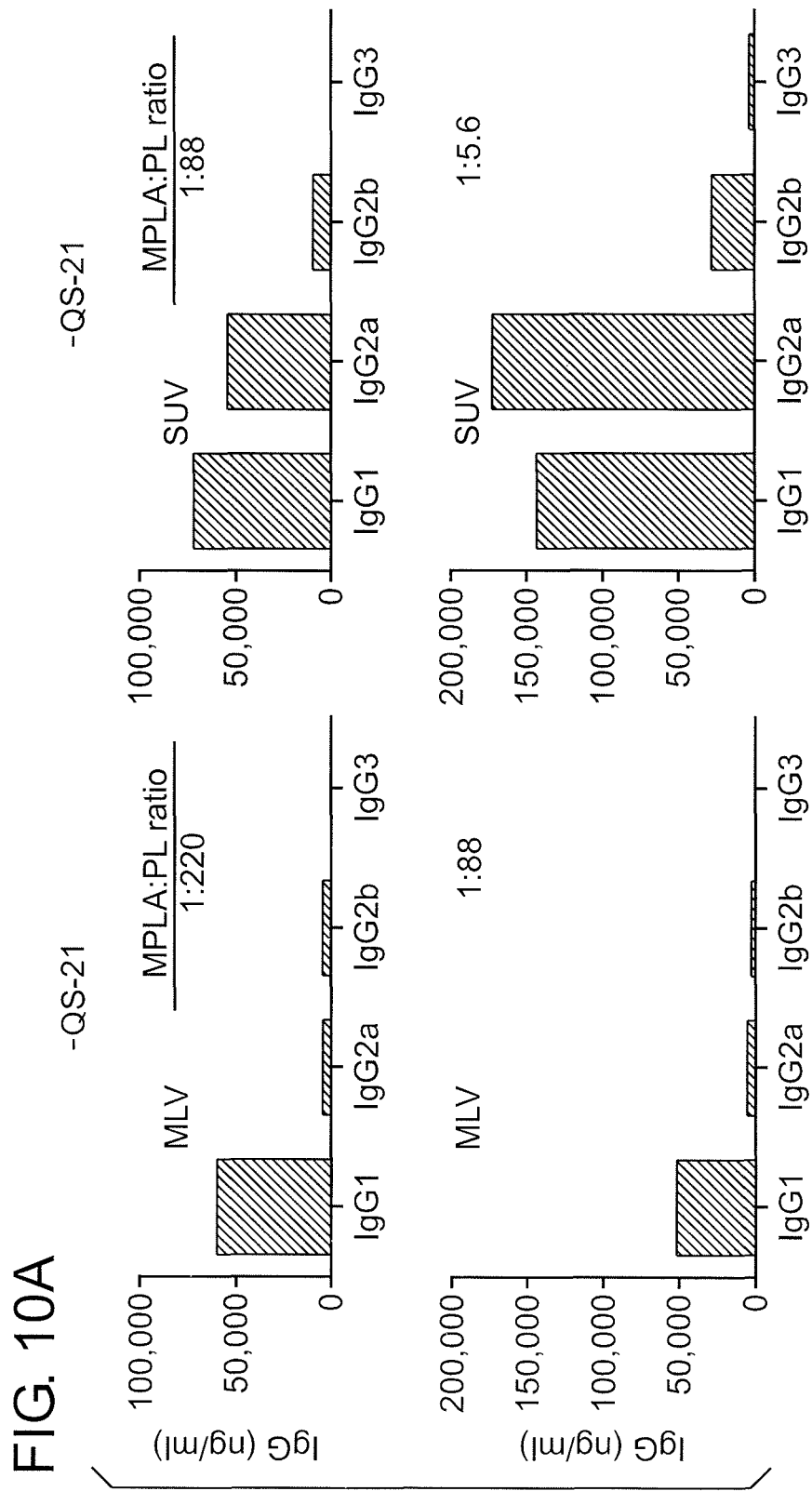
FIG. 10 depicts IgG subtype profiles of anti-gp140 antisera as described in Example 4 and Materials and Methods. Mice were immunized with ALF+gp140 (FIG. 10A) or ALFQ+gp140 (FIG. 10B). ELISA plates were coated with gp140. Subtype analyses were conducted and values were calculated from standard curves. Each panel represents pooled sera from one group from week 9 of immunized mice.
Figure 10B:
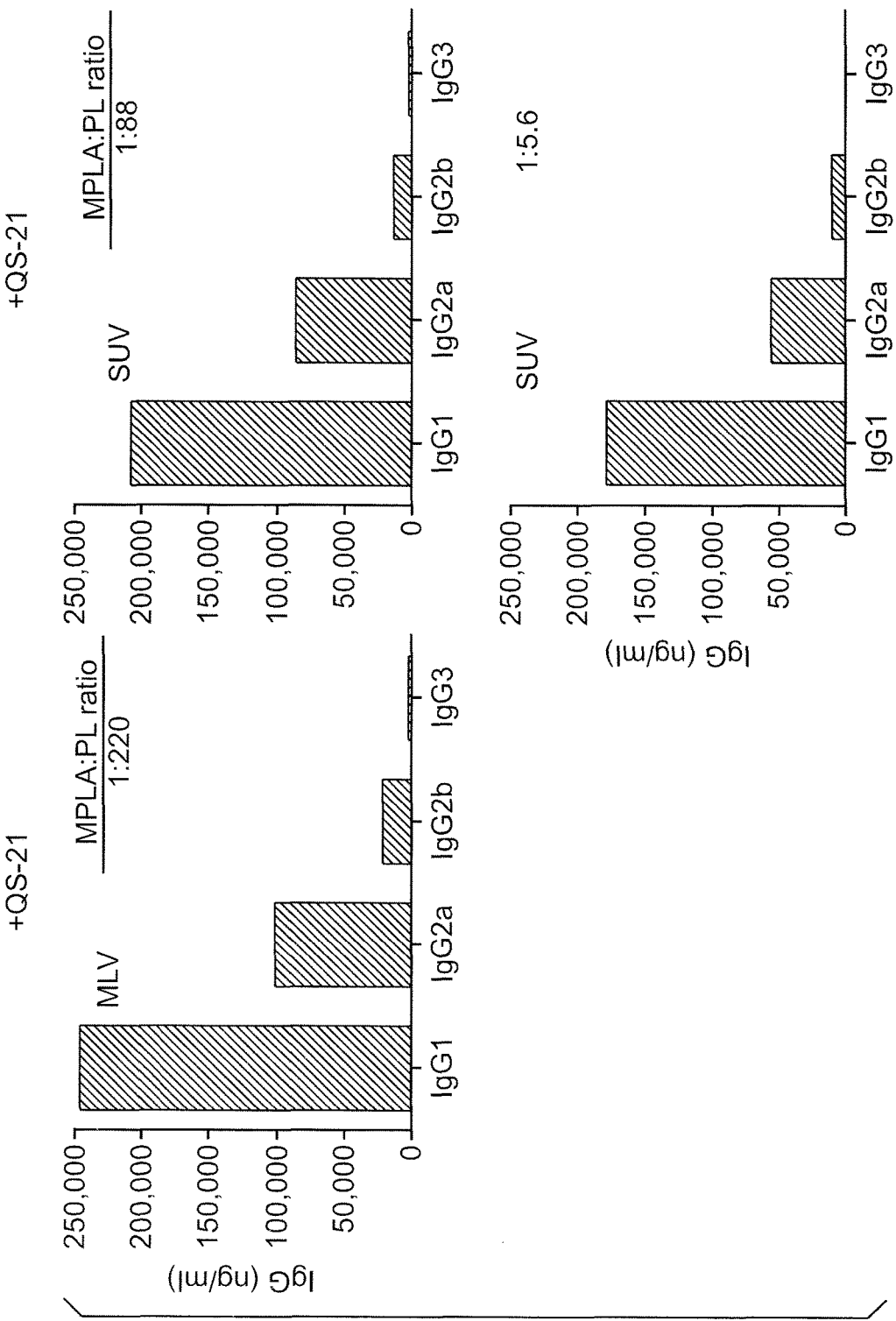

IgG subtype determination was conducted to further characterize the antibody production. All mouse groups immunized with ALF+gp140 revealed moderate or high titers of IgG1 binding antibodies to gp140 (FIG. 10A). ALF MLV induced dominantly IgG1 subclass, while ALF SUV induced a balance between IgG1 and IgG2a production and also induced IgG2b production. Increasing the MPLA:phospholipid ratio resulted in higher antibody responses of all subclasses (FIG. 10A). As shown in FIG. 10B, in the ALFQ groups the serum concentration of IgG1 was constantly high; and all subtypes were induced, but these were independent of the MPLA:phospholipid ratios of ALF SUV or ALF MLV initially utilized for creation of ALFQ.

Figure 11A:
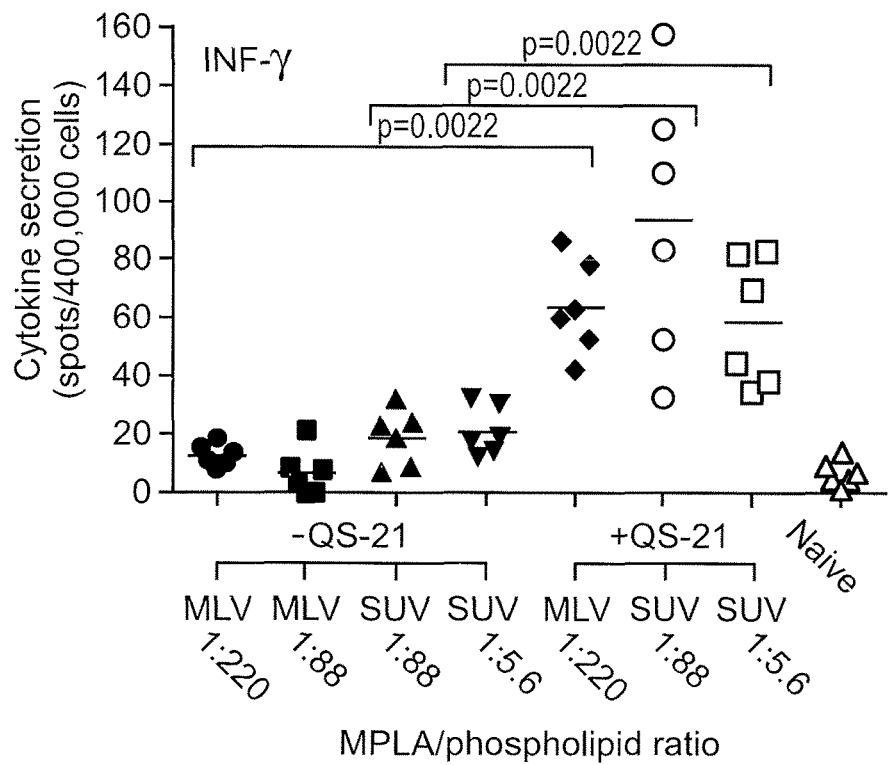
FIG. 11 depicts production of IFN-γ (FIG. 11A) and IL-4 (FIG. 11B) by splenocytes from mice 9 weeks after primary immunization. Splenocytes were plated and stimulated with gp140 CN54 for 18 hours, and the number of cytokine producing cells were determine by ELISPOT. Vertical lines represent the mean of the 6 animals/group (Naïve: non-immunized control mice).
Figure 11B:
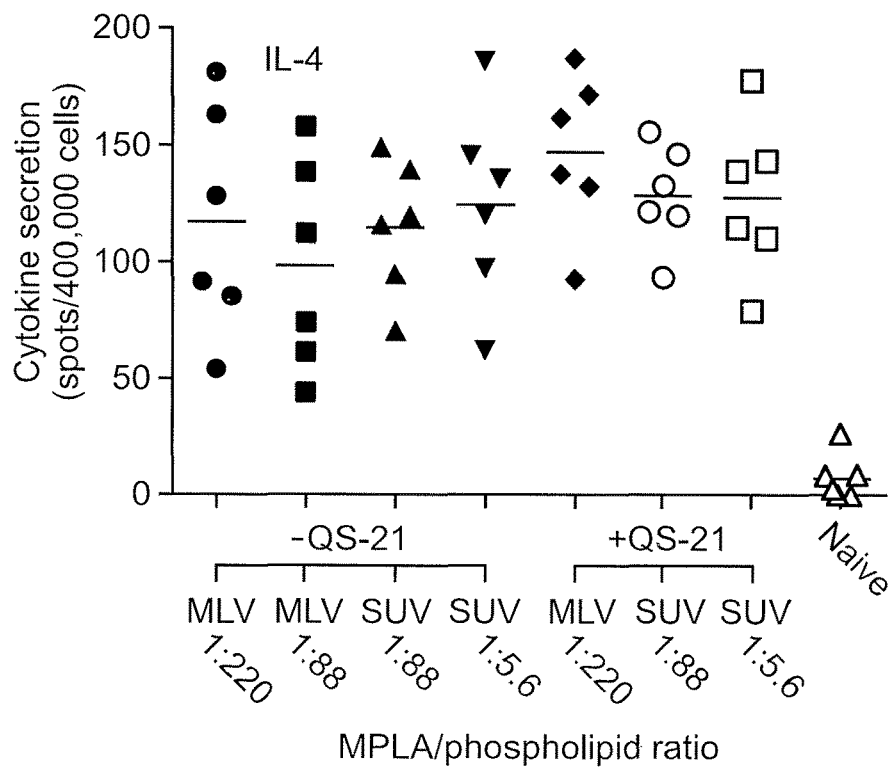

In order to compare Th1 vs. Th2 immune responses, ELISPOT analyses were performed on freshly isolated splenic lymphocytes from mice immunized with adjuvanted gp140. As shown in FIG. 11, all of the ALF-adjuvanted formulations induced proliferation of INF-γ-producing splenic lymphocytes that was higher than observed with the naïve control. ALFQ formulations induced significantly higher numbers of INF-γ-positive cells than ALF (FIG. 11A). All of the immunized mice exhibited high IL-4 production that was significantly higher ($p<0.0001$) than naïve mice (FIG. 11B). Significant differences of IL-4 producing cell numbers were not observed among immunized groups. Given the above results, it appeared that the ALFQ liposomes caused a distinctive induction of INF-γ secretion that was independent of the MPLA:phospholipid ratio. Thus, the ALFQ liposomes might be a potentially useful adjuvant for induction of Th1-type immunity.

Figure 12A:
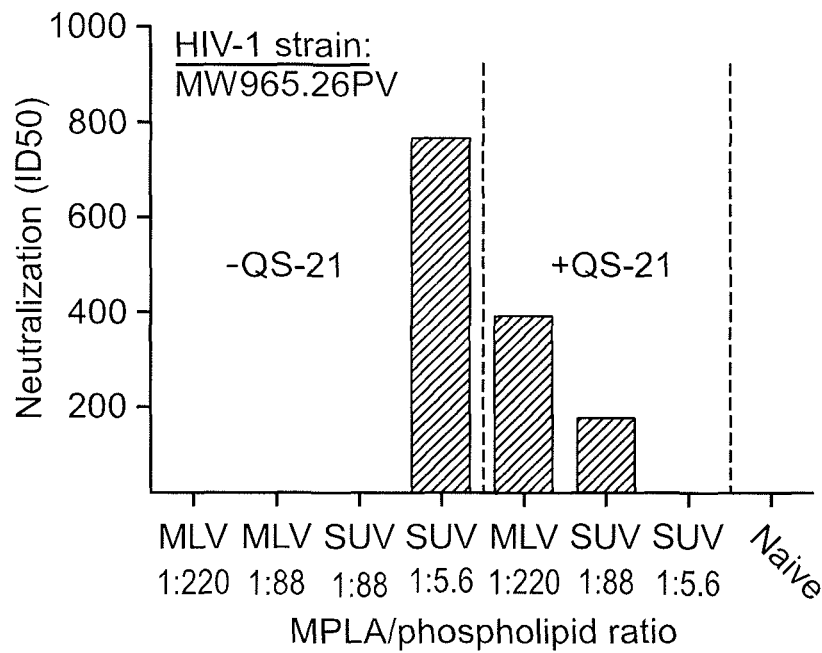
FIG. 12 depicts neutralization of HIV by pooled antisera. The vaccine formulation is indicated on the x-axis. ID50 values represent 50% neutralization of pseudoviruses MW965.26PV (FIG. 12A) and GS015PV (FIG. 12B) at the indicated dilution of the serum samples from mice 9 weeks after primary immunization. The controls were sera from non-immunized mice. ID50 values <20 were considered as background. MuLV PV was used as assay negative control (data not shown).
Figure 12B:
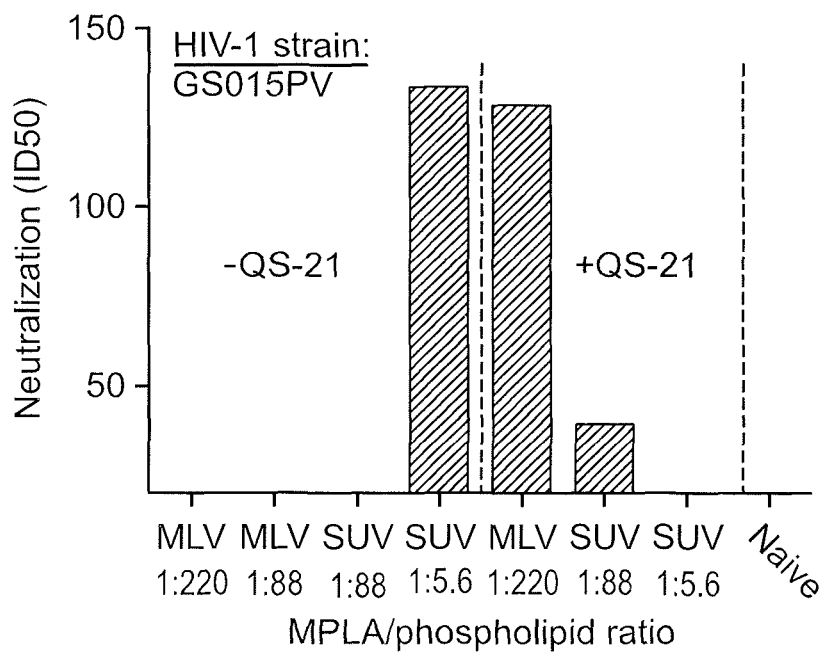

Although non-neutralizing binding antibodies to HIV-1 envelope protein were reported to be correlated with protection in a phase III efficacy trial, neutralizing antibodies are widely viewed as being important for a prophylactic vaccine to HIV-1. Because of this, the ability of ALF and ALFQ to serve as adjuvants to induce neutralizing antibodies to a model gp140 envelope protein was examined. Pooled serum samples of the mouse groups were tested against two tier 1, clade C HIV primary isolates. As shown in FIG. 12, one ALF-adjuvanted and two ALFQ-adjuvanted vaccine groups induced anti-gp140 antisera that neutralized both MW965.26PV (FIG. 12A) and GS015PV (FIG. 12B) at high ID50. ALF having an MPLA:phospholipid ratio of 1:5.6 induced the highest neutralization titer, while ALFQ with 1:88 and 1:220 MPLA:phospholipid ratios also induced neutralizing antibodies, but with somewhat lower titers.

What is claimed is:

1. An adjuvant formulation comprising unilamellar liposomes having a liposome bilayer that consists of:
   (a) at least one phosphatidylcholine (PC) and/or phosphatidylglycerol (PG), as phospholipids, selected from the group consisting of: dimyristoyl phosphatidylcholine (DMPC), dipalmitoyl phosphatidylcholine (DPPC), distearyl phosphatidylcholine (DSPC), dimyristoyl phosphatidylglycerol (DMPG), dipalmitoyl phosphatidylglycerol (DPPG), and distearyl phosphatidylglycerol (DSPG);
   (b) cholesterol;
   (c) monophosphoryl lipid A (MPLA); and
   (d) a saponin; and
   wherein the mole ratio of the cholesterol (b) to the phospholipids (a) is greater than about 50:50; and
   wherein the unilamellar liposomes have a median diameter size in micrometer range as detected by light scattering analysis.

2. The adjuvant formulation of claim 1, wherein the saponin is QS-7, QS-18, QS-21, or a mixture thereof.

3. The adjuvant formulation of claim 1, wherein the saponin is QS-21.

4. The adjuvant formulation of claim 1, wherein the mole ratio of the cholesterol (b) to the phospholipids (a) is about 55:45 to about 71:29.

5. The adjuvant formulation of claim 1, wherein the mole ratio of the cholesterol (b) to the phospholipids (a) is about 55:45.

6. The adjuvant formulation of claim 1, wherein dimyristoyl phosphatidylcholine (DMPC) is selected as a phospholipid.

7. The adjuvant formulation of claim 6, wherein additionally dimyristoyl phosphatidylglycerol (DMPG) is selected as a phospholipid.

8. The adjuvant formulation of claim 1, wherein both a PC and a PG are selected as phospholipids, and wherein the ratio of the PC to the PG (mol/mol) is about 0.5:1, about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1.

9. A liposome suspension comprising the adjuvant formulation of claim 1 and phosphate-buffered saline (PBS), pH 7.4, wherein the liposome suspension comprises (i) 1.272 mM to 50 mM of the phospholipids (a), and (ii) about 5 mg/ml or less of the MPLA (c).

10. The adjuvant formulation of claim 1, wherein the mole ratio of the MPLA (c) to the phospholipids (a) is about 1:5.6 to about 1:880.

11. A liposome suspension comprising the adjuvant formulation of claim 1 and phosphate-buffered saline (PBS), pH 7.4, wherein the liposome suspension comprises (i) 1.272 mM to 50 mM of the phospholipids (a), and (ii) about 1 mg/ml or less of the saponin (d).

12. An immunogenic composition comprising an immunogen and the adjuvant formulation of claim 1.

13. The immunogenic composition of claim 12, further comprising a physiologically acceptable vehicle.

14. The immunogenic composition of claim 12, wherein the immunogen is selected from the group consisting of a naturally-occurring or artificially-created protein, a recombinant protein, a glycoprotein, a peptide, a carbohydrate, a hapten, a whole virus, a bacterium, a protozoan, and a virus-like particle.

15. The immunogenic composition of claim 14, wherein the immunogen is an HIV-1 envelope protein.

16. The adjuvant formulation of claim 10, wherein the mole ratio of the MPLA (c) to the phospholipids (a) is about 1:88 to about 1:220.

* * * * *